United States Patent
Bond-Thorley et al.

(10) Patent No.: US 9,885,690 B2
(45) Date of Patent: Feb. 6, 2018

(54) RADIUS INSPECTION TOOLS

(71) Applicant: AIRBUS OPERATIONS LIMITED, Bristol (GB)

(72) Inventors: Andrew Bond-Thorley, Stonehouse (GB); Neil Hankinson, Warrington (GB); Richard Freemantle, Ashbourne (GB)

(73) Assignee: AIRBUS OPERATIONS LIMITED, Bristol (GB)

(*) Notice: Subject to any disclaimer, the term of this patent is extended or adjusted under 35 U.S.C. 154(b) by 296 days.

(21) Appl. No.: 14/420,436

(22) PCT Filed: Aug. 1, 2013

(86) PCT No.: PCT/GB2013/052059
§ 371 (c)(1),
(2) Date: Feb. 9, 2015

(87) PCT Pub. No.: WO2014/023938
PCT Pub. Date: Feb. 13, 2014

(65) Prior Publication Data
US 2015/0219602 A1    Aug. 6, 2015

(30) Foreign Application Priority Data
Aug. 9, 2012  (GB) .................... 1214273.3

(51) Int. Cl.
*G01N 29/22* (2006.01)
*G01N 29/24* (2006.01)

(52) U.S. Cl.
CPC .......... *G01N 29/24* (2013.01); *G01N 29/221* (2013.01); *G01N 2291/106* (2013.01)

(58) Field of Classification Search
CPC . G01N 29/221; G01N 29/24; G01N 2291/106
USPC ......................................... 73/632
See application file for complete search history.

(56) References Cited

U.S. PATENT DOCUMENTS

| 4,509,815 A | 4/1985 | Fischer et al. |
| 4,796,632 A * | 1/1989 | Boyd ............... A61B 8/4281 600/459 |
| 7,284,434 B1 | 10/2007 | Fleming |
| 8,012,095 B2 * | 9/2011 | Prager .................. A61B 8/10 600/459 |
| 8,087,298 B1 * | 1/2012 | DiMambro .......... G01N 29/226 73/629 |
| 2006/0027022 A1 | 2/2006 | Flora et al. |

(Continued)

FOREIGN PATENT DOCUMENTS

| EP | 1312423 A1 | 5/2003 |
| FR | 2669430 A1 | 5/1992 |

(Continued)

OTHER PUBLICATIONS

International Search Report dated Mar. 24, 2014 in International Application No. PCT/GB2013/052059, filed Aug. 1, 2013.

(Continued)

*Primary Examiner* — J M Saint Surin
(74) *Attorney, Agent, or Firm* — Hauptman Ham, LLP (57) ABSTRACT

An ultrasonic inspection tool has a chassis with a two part body, an aperture for providing a clear line of sight between an array and a workpiece, and a series of feet for sliding along the workpiece.

18 Claims, 6 Drawing Sheets

(56) References Cited

U.S. PATENT DOCUMENTS

2008/0255455 A1* 10/2008 Sokulin .................. A61B 8/08
                                                    600/459
2011/0072904 A1    3/2011 Lam et al.
2011/0303013 A1* 12/2011 Kass ...................... G01N 29/28
                                                    73/632

FOREIGN PATENT DOCUMENTS

| GB | 201018259    | * 12/2010 |
|----|--------------|-----------|
| WO | 2006/014714 A2 | 2/2006  |
| WO | 2008/157665 A1 | 12/2008 |
| WO | 2010/107637 A2 | 9/2010  |
| WO | 2012/031988 A1 | 3/2012  |
| WO | 2012/056218 A1 | 5/2012  |

OTHER PUBLICATIONS

Written Opinion dated Mar. 24, 2014 in International Application No. PCT/GB2013/052059, filed Aug. 1, 2013.
UKIPO Search Report dated Nov. 7, 2012 in Great Britain Application No. 1214273.3, claims 1-9.
UKIPO Search Report dated Jan. 10, 2013 in Great Britain Application No. 1214273.3, claims 10-16.
UKIPO Search Report dated Jan. 10, 2013 in Great Britain Application No. 1214273.3, claims 17-22.
UKIPO Search Report dated Jan. 10, 2013 in Great Britain Application No. 1214273.3, claims 23-25.

* cited by examiner

RADIUS INSPECTION TOOLS

RELATED APPLICATIONS

The present application is a National Phase of International Application Number PCT/GB2013/052059, filed Aug. 1, 2013, and claims priority from Great Britain Application Number 1214273.3, filed Aug. 9, 2012.

The present invention is concerned with an improved ultrasonic inspection tool. More specifically, the present invention is concerned with an ultrasonic inspection tool which utilises a flexible array in order to account for variability in the dimensions of radiused components.

By radiused components, we mean components having a curved or circle-segment cross-section. Such components often comprise a radiused portion extending through 90 degrees with a planar flange extending from either end thereof, perpendicular to each other. Aircraft components such as stringers and wing spars are examples of radiused components.

Composite radiused components may experience various features within the radius. For example, fibre waviness, delamination and porosity may detrimentally affect the mechanical properties of the material. As such, increase in material thickness has to be designed-in to account for this which increases the weight and cost of the component. This is undesirable.

Traditional methods of detecting such features involve providing a rigid curved array of ultrasonic elements directed normal to the surface of the component in order to detect any features therein. By "array" we mean a series of ultrasonic transducers which are controlled so as to work co-operatively in scanning a workpiece, e.g., through beam focussing or steering. A typical ultrasonic array comprises a series of piezoelectric transducers attached to a substrate to maintain their relative positions.

In many applications, and in particular in the aerospace sector, both the radius of the component and the "opening angle" (i.e. the angle between the flanges extending from either end of the radiused portion) varies along the length of the component. This may occur intentionally due to the shape of the component, or unintentionally due to manufacturing tolerances. Either way, this often causes problems for known array probes because variations in the dimensions of the component may produce inaccurate results as the ultrasonic pulses do not enter and exit the material in the expected manner. The array couplant may also lose contact with the workpiece as the shape of the workpiece changes.

In addition, should a user wish to inspect a wide range of radiused components with varying radii and opening angles, then generally that user has to use a different probe. This is expensive and means that a significant number of array probes must be kept in store to cope with variations in component dimensions.

A known inspection device is disclosed in the applicant's published application WO2012/056218. This document discloses a flexible array probe and an apparatus for scanning a radiused workpiece.

One problem with the device of WO'218, is that the user has to feed the flexible array into the coupling component from the end. This can be difficult and time consuming.

A further problem with the device of WO'218 is that in order to effectively ultrasonically couple the array to the workpiece, a separate water supply is required to create a water film between the coupling component and the workpiece. The transition of ultrasonic energy from the array through the couplant, through a water film and into the workpiece may also result in a degradation of signal quality, as there are several material boundaries to cross.

The coupling component of WO'218 is constructed from a material with a low ultrasonic attenuation (rubber). generally, such materials are ideal for sliding along the workpiece as the coefficient of friction between the workpiece and the component is high.

WO'218 also discloses that the flexible array is positioned near the top of the coupling component. This can be problematic as local pressure on piezoelectric array elements in particular, can detrimentally affect their signal properties.

It is an aim of the present invention to overcome, or at least mitigate, one of the above problems.

According to a first aspect of the invention there is provided an ultrasonic inspection probe comprising:
  a flexible ultrasonic array; and,
  a chassis arranged to hold the ultrasonic array in a predetermined position relative to the workpiece, the chassis having a workpiece facing surface and a chassis loading surface opposite thereto, the ultrasonic array disposed between the workpiece facing surface and the chassis loading surface;
  in which the chassis comprises a first component defining the workpiece facing surface and a second component defining the chassis loading surface, the first and second components being releasably attached for insertion and removal of the ultrasonic array therebetween.

Advantageously, this simplifies the loading and unloading of the array into the chassis, improving the case of changing chassis or array depending on the application.

Preferably the workpiece facing surface and the first and second components are at least partially curved to scan curved components.

Preferably the first and second components clamp the ultrasonic array therebetween. Advantageously, this forces the array to conform to the shape of the chassis and therefore the workpiece, especially if the chassis deforms in use.

The first and second components may be configured to be snap-fitted together.

Preferably the chassis defines an aperture in the workpiece facing surface to provide a clear line of sight from the array to the workpiece. Preferably the aperture is surrounded by a deformable sealing material, which may be a closed cell foam such as neoprene.

Preferably the chassis defines couplant channels arranged to direct liquid couplant to the workpiece facing surface. This avoids the need for a separate couplant supply, and ensures that couplant is provided between the array and the workpiece.

Preferably the couplant channels are arranged to direct liquid to the aperture.

According to a second aspect of the invention there is provided an ultrasonic inspection probe comprising:
  a flexible ultrasonic array; and,
  a chassis arranged to hold the ultrasonic array in a predetermined position relative to the workpiece, the chassis having a workpiece facing surface and a chassis loading surface opposite thereto, the ultrasonic array disposed between the workpiece facing surface and the chassis loading surface;
  in which the chassis defines an aperture in the workpiece facing surface, the aperture disposed between the ultrasonic array and the workpiece to provide a clear line of sight between the array and the workpiece.

By "clear line of sight" we mean that no solid components sit between the array and workpiece in use. Fluids, such as couplant liquid, may be introduced into the aperture but a "clear line of sight" remains present.

Advantageously, the chassis performs the function of controlling the shape of the array, but a clear line of sight is established to the workpiece which reduces the number of material boundaries found in the prior art.

A liquid injection system may be provided, configured to direct liquid couplant to the aperture. The liquid injection system may comprise a series of channels formed in the chassis. Preferably, the liquid injection system comprises a series of outlets exiting into the aperture.

Preferably the aperture is surrounded by a deformable sealing material, which may be a closed cell foam such as neoprene.

Preferably the seal is an endless loop surrounding the aperture.

According to a third aspect of the invention there is provided an ultrasonic inspection probe comprising:
  a flexible ultrasonic array; and,
  a chassis arranged to hold the ultrasonic array in a predetermined position relative to the workpiece, the chassis having a main body defining a workpiece facing surface and a chassis loading surface opposite thereto, the ultrasonic array disposed between the workpiece facing surface and the chassis loading surface;
  in which the chassis at least one foot protruding from the workpiece facing surface of the main body.

Advantageously, the properties of the foot material can be chosen to ensure that sliding can easily take place between the probe and the workpiece, whilst the material choice for the chassis can be completely dependent on its desired mechanical properties (e.g. deformability).

Preferably the at least one foot is constructed from a material having a lower coefficient of friction than the main body. The at least one foot may constructed from a polymer such as polyoxymethylene or PTFE.

Preferably the foot or feet are configured to provide an offset between the workpiece facing surface and workpiece in use.

Preferably the chassis has a seal member protruding from the workpiece facing surface of the main body, the seal member arranged to seal against a workpiece in use, wherein a thickness of the foot normal to the workpiece facing surface is less than a thickness of the seal member such that the sealing material is compressed against the workpiece in use. This ensures a good seal with the workpiece.

Preferably the seal member is an endless loop defining a cavity between the workpiece facing surface and workpiece in use. This cavity can then be filled with liquid couplant. Preferably the flexible ultrasonic array is arranged to emit ultrasonic energy towards the cavity.

Preferably the main body defines an aperture in the workpiece facing surface, which aperture is surrounded by the seal member.

According to a fourth aspect of the invention there is provided an ultrasonic inspection probe comprising:
  a flexible ultrasonic array; and,
  a chassis arranged to hold the ultrasonic array in a predetermined position relative to the workpiece, the chassis having a workpiece facing surface and a chassis loading surface opposite thereto, the ultrasonic array disposed between the workpiece facing surface and the chassis loading surface;
  in which in a cross section perpendicular to the workpiece facing surface the ultrasonic array is closer to the workpiece facing surface than the loading surface.

Preferably the ultrasonic array is more than 60 percent through the thickness of the chassis, more preferably the ultrasonic array is more than 80 percent through the thickness of the chassis.

Any of the above aspects of the invention can be combined, as demonstrated by the examples below.

An example ultrasonic inspection probe will now be described with reference to the following figures.

A first ultrasonic inspection probe 100 is shown in FIGS. 1 to 4d. The probe 100 comprises a chassis 102, a first handle 104, a second handle 106 and a rotary encoder 108. The chassis 102 comprises a body 116 which is generally curved in cross-section and prismatic. The body 116 comprises a first planar portion 110, a 90 degree radiused portion 112 and a second planar portion 114. The planar portions 110, 114 extend from either end of the radiused portion 112.

Figure 1:
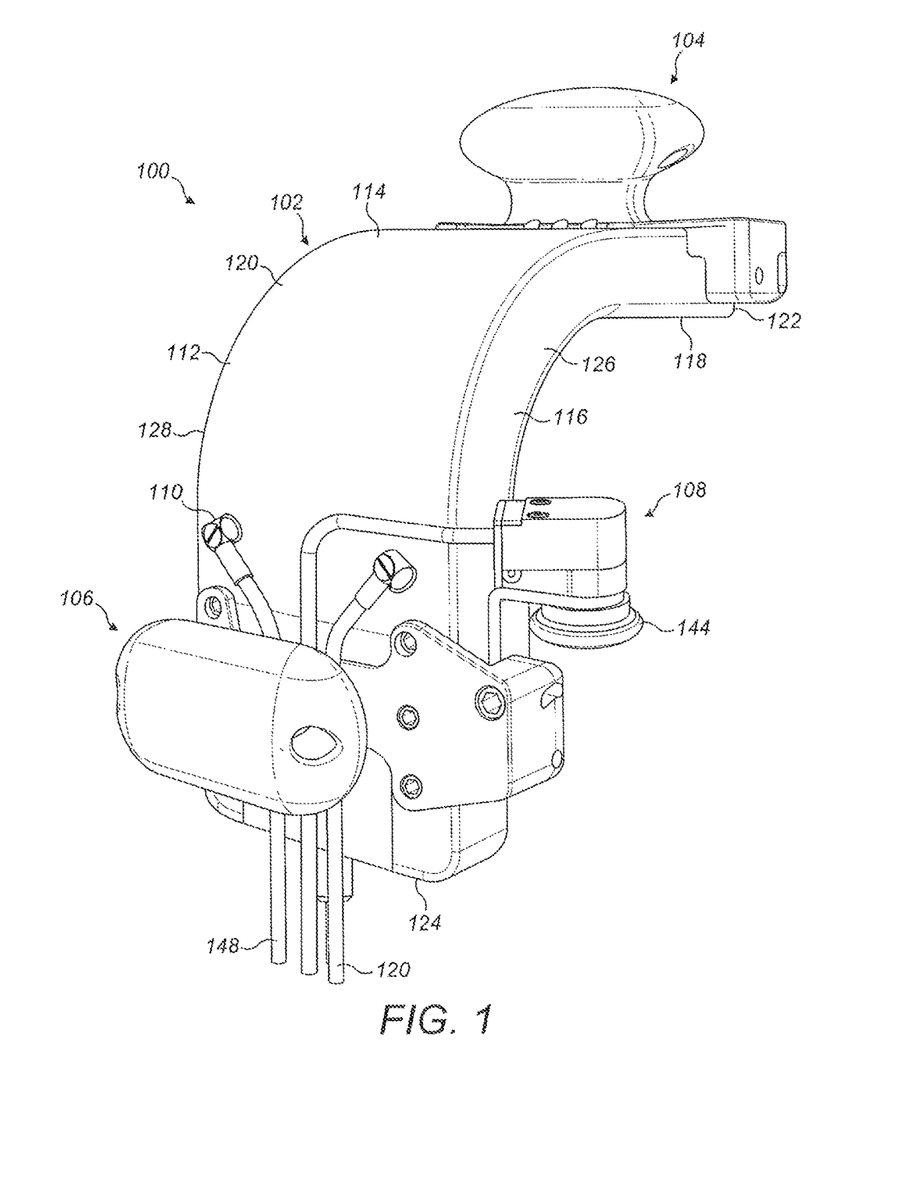
FIG. 1 is a perspective view of a first ultrasonic inspection probe in accordance with the present invention.
Figure 2:
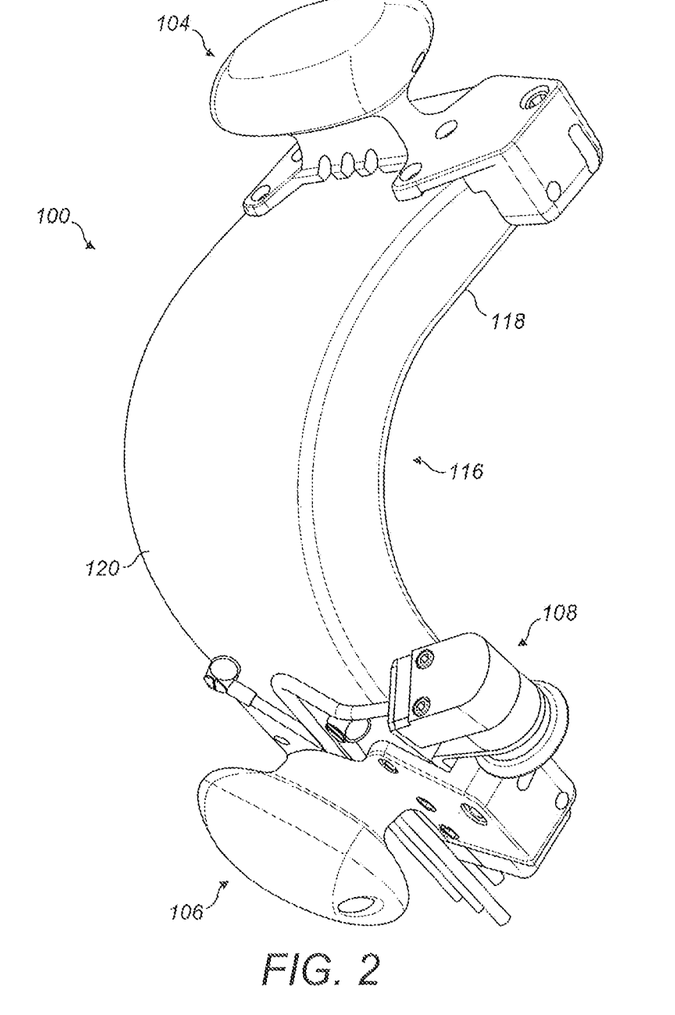
FIG. 2 is a second perspective view of the probe of FIG. 1.

The probe 100 is configured to be moved along an elongate radiused workpiece in an axial direction of the radiused portion 112. The terms "axial" and "radial" from hereon in will be used in respect of the radiused portion 112.

The main body 116 defines a workpiece facing surface 118 on one side and a chassis loading surface 120 on the opposite side. In the embodiment shown, the main body 116 has a concave workpiece facing surface suitable for addressing a convex workpiece. It will be understood that the main body 116 could define a convex workpiece facing surface for scanning a concave workpiece.

The main body 116 defines a first end 122 and a second end 124, as well as side walls 126, 128. The main body 116 is of two part construction (as will be described below) and defines a central cavity for receiving an ultrasonic array 146.

Figure 3:
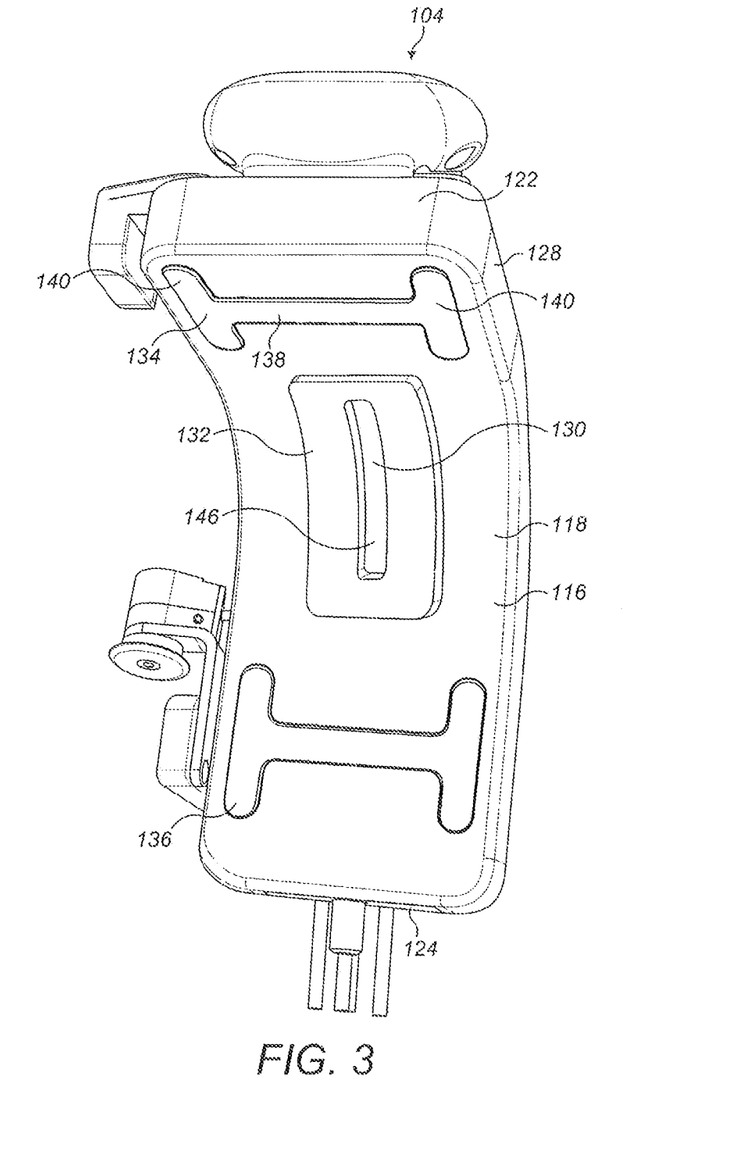
FIG. 3 is an underside perspective view of the probe of FIG. 1.

Turning to FIG. 3, on the workpiece facing surface 118 of the main body 116, an aperture 130 is defined. The aperture 130 extends longitudinally along the body 116 and is open to the array-containing cavity of the main body 116 as will be described below.

Surrounding the aperture 130 there is provided an endless liquid seal 132 constructed from neoprene.

Two feet 134, 136 are provided at either end of the body 116 on the workpiece facing surface 118. The first foot 134 is provided proximate the first end 122 and the second foot 136 is provided proximate the second end 124. Each of the feet 134, 136 is substantially identical and, as such, only the foot 134 will be described here. The foot 134 is substantially "H" shaped having a transverse portion 138 spanning the width of the main body 116, terminating in two perpendicular longitudinal portions 140, 142, forming an "H" shape. The feet 134, 136 are positioned at either end of the aperture 130 and extend the entire width of the aperture 130 and seal 132 in the axial direction. In fact, the feet 134, 136 are configured such that the transverse portions 138 are wider than the seal 132 in the axial direction. This ensures that the seal 132 is uniformally compressed against the workpiece (as will be described below).

The first and second handles 104, 106 are identical and positioned near the first and second ends 122, 124 of the body 126 respectively. The handles 104, 106 are positioned opposite the feet 134, 136 respectively such that there is a straight and direct radial load path from the handles 104, 106 into the feet 134, 136. Each handle 104, 106 is configured so that a user can apply pressure onto the chassis loading surface 120 through the body 116 and thereby apply pressure across the workpiece facing surface 118 to ensure that the surface 118 is urged towards the workpiece such that the seal 132 can abut the workpiece and seal the aperture 130.

The rotary encoder 108 is generally known in the art and comprises an encoder wheel 144, which is arranged to rotate as the probe 100 is moved along the length of a radiused component or workpiece.

The main body 116 is a two part component defining a cavity therein. A flexible array 146 installed within the cavity and is exposed to the workpiece through the aperture 130 in the workpiece facing surface 118. The body 116 is constructed from a flexible material so it can conform to the changing shape of the workpiece.

As will be described below, within the body 116 there is provided a plurality of fluid channels into which water can be introduced via liquid inputs 148, 150. The liquid is channeled into the aperture 130. As such, a fluid filled cavity is formed between the array 146 and the workpiece. The neoprene liquid seal 132 slows the egress of water from the cavity defined by the aperture 130. As such, good ultrasonic coupling is provided between the array 146 and the workpiece by the presence of a water filled cavity.

Turning to FIGS. 4a to 4d, schematic views of the array 100 are shown.

Figure 4A:
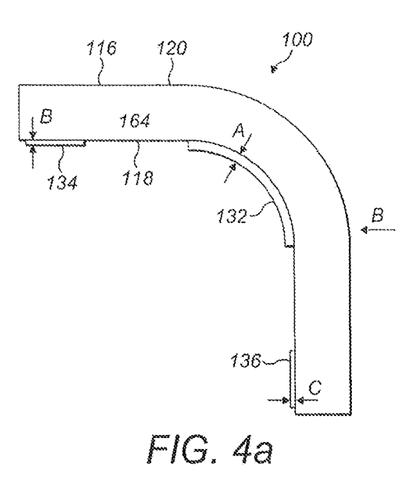
FIG. 4a is a schematic side view of the ultrasonic inspection probe of FIG. 1.
Figure 4B:
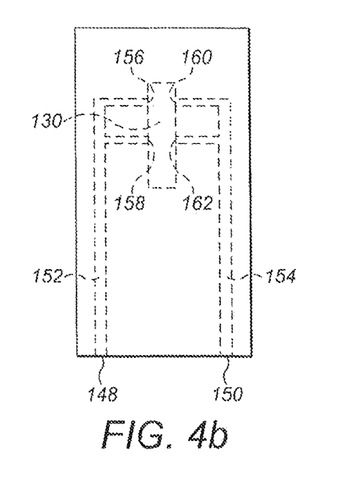
FIG. 4b is a schematic end view of the probe of FIG. 1.

Turning to FIG. 4b, which is a view in direction B of FIG. 4a, the fluid channels leading to the aperture 130 are shown in hidden lines. Two fluid inputs 148 and 150, lead through a system of channels 152, 154 respectively, to exit at orifices 156, 158, 160 and 162 into aperture 130.

It will be noted in FIG. 4a that the neoprene liquid seal 132 has a thickness A extending from the workpiece facing surface 118. Each of the feet 134, 136 has thickness B and C respectively. In order to provide a good seal between the aperture 130 and the workpiece surface, dimensions B and C (which are equal) are less than the thickness A of the neoprene. As such, when a user applies pressure to the body 116, the neoprene 132 is compressed and forms a good seal with the workpiece.

Figure 4C:
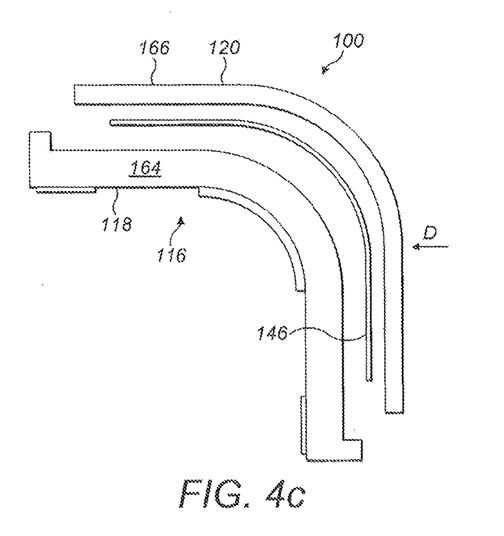
FIG. 4c is a schematic side exploded view of the probe of FIG. 1.

Turning to FIG. 4c, the probe 100 is shown in exploded view in which the body 116 is shown to comprise a base part 164 defining the workpiece facing surface 118 and a lid 166 defining the chassis loading surface 120. The lid 166 is removable in order to expose an inner cavity of the body 116 for insertion of the ultrasonic array 146. The lid 166 and base part 164 snap fit together to clamp the flexible array 146 therebetween.

Figure 4D:
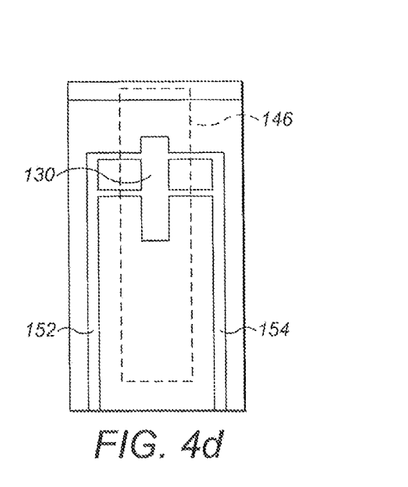
FIG. 4d is a schematic end view of the part of the probe of FIG. 1.

Turning to FIG. 4d, a view in direction D of the body 116, absent both the lid 166 and the array 146, is shown. As can be seen, the various channels 152, 154 are formed in the upper surface of the base part 164 opposite the workpiece facing surface 118 and are exposed by removal of the lid 166. When installed, the lid 166 closes the channels 152, 154. An outline of the array 146 is also shown, demonstrating that it overlaps the aperture 130 in order to have a clear "line of sight" to the workpiece in use.

In use, the probe 100 is placed with the seal 132 and feet 134, 136 in contact with a workpiece. Liquid couplant is introduced into the cavity 130. The probe 100 is then moved in an axial direction to scan the workpiece along its length. The encoder 108 measures the distance traveled and allows a "map" of the workpiece to be created.

Figure 5:
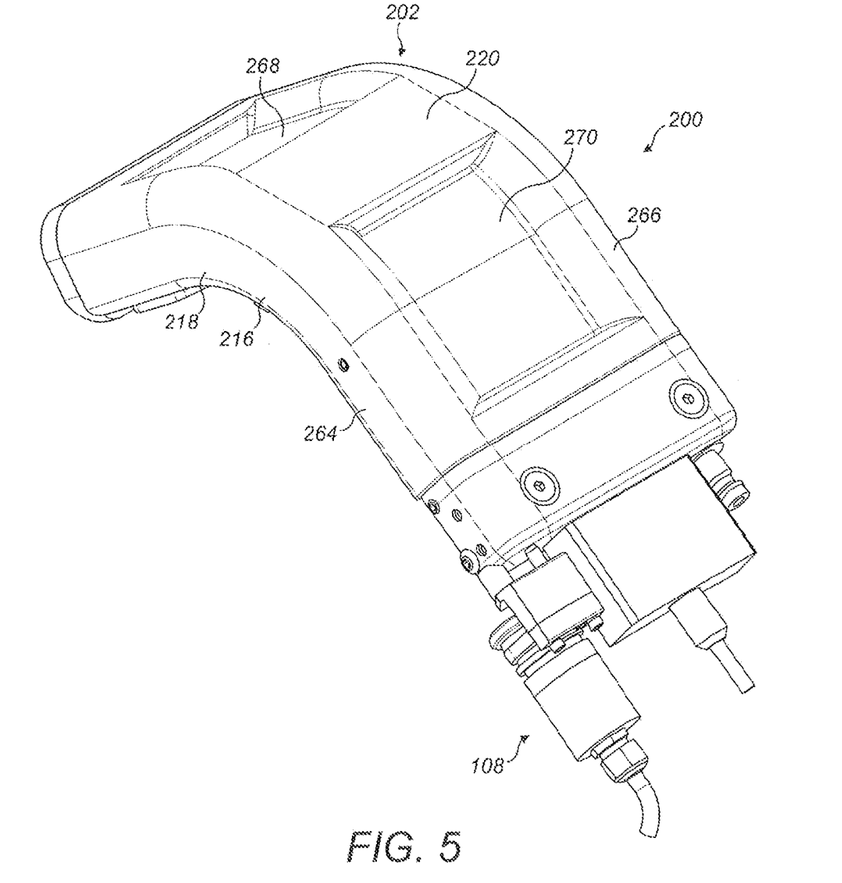
FIG. 5 is a perspective view of a second ultrasonic inspection probe in accordance with the present invention.
Figure 6:
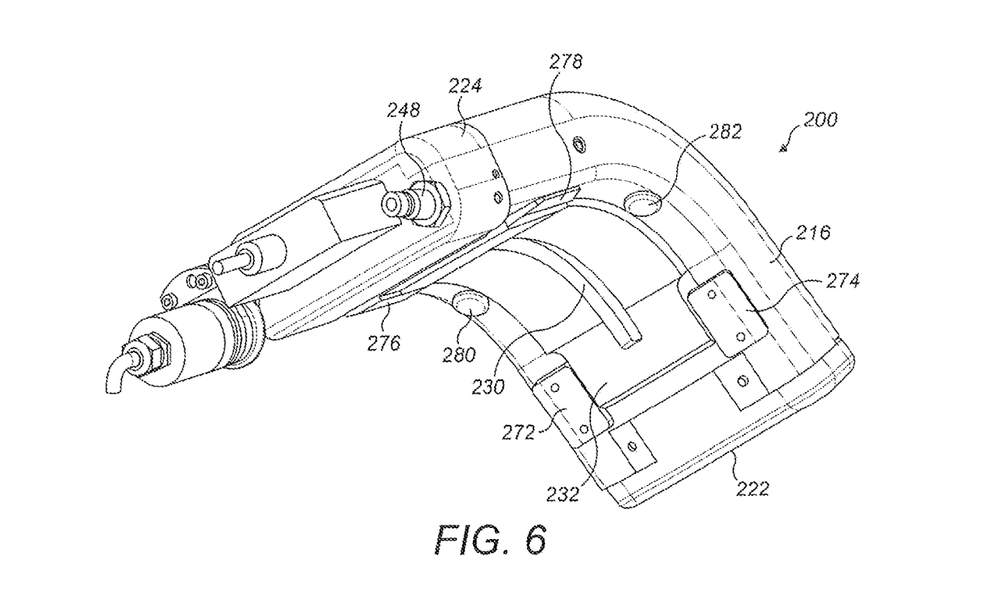
FIG. 6 is an underside perspective view of the probe of FIG. 5.
Figure 7:
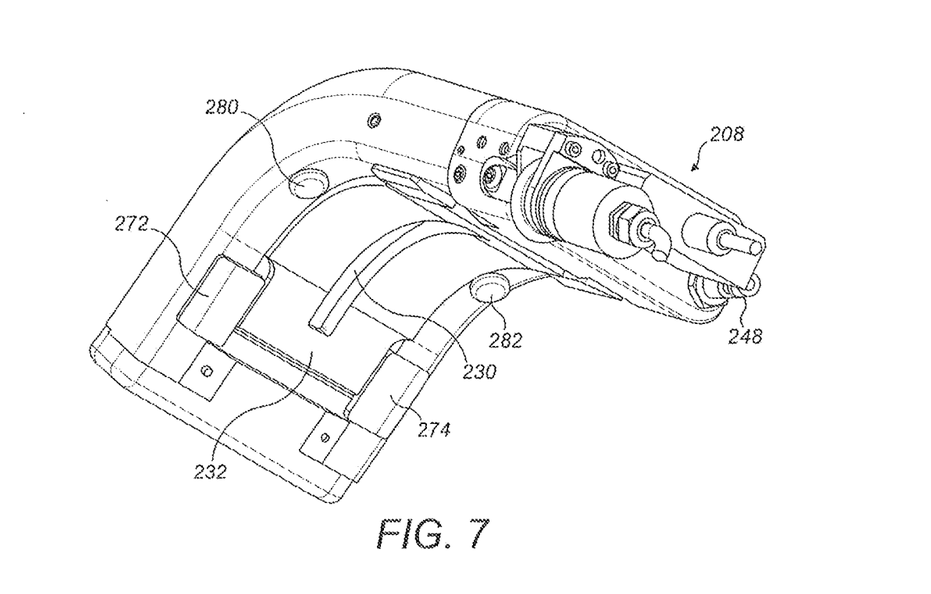
FIG. 7 is an underside perspective view of the probe of FIG. 5.

Turning to FIGS. 5 to 7, a second ultrasonic inspection probe 200 in accordance with the present invention is shown. The operating principles of the second probe 200 are substantially the same as the first probe 100. Like the first probe 100, the second probe 200 comprises a chassis 202 as well as an encoder 208. The probe 200 does not have handle portions and is configured for direct application of pressure by an operator's hand.

Like the probe 100, the chassis 202 of the probe 200 defines a main body 216 having a base part 264 and a lid 266 which is removable to expose a cavity for the insertion of a flexible, ultrasonic array.

The body 216 defines a workpiece facing surface 218, and a chassis loading surface 220 opposite thereto. The chassis loading surface 220 defines a pair of recesses 268, 270 which aid the user in applying a lateral force on the probe 200 when sliding it along a workpiece.

Referring to FIG. 6, the underside of the probe 200 is shown. Like the probe 100, the workpiece facing surface 218 defines an aperture 230 in order to provide the ultrasonic array with direct line of sight to the workpiece. Surrounding the aperture 230 there is provided a neoprene liquid seal 232. Proximate a first end 222 of the body 216, there are provided two opposed feet 272, 274 which are constructed from a low friction material, such as PTFE. Similarly, proximate the second end 224, there are provided further two feet 276, 278. At the apex of the curved portion of the body 216 there are provided a still further two feet 280, 282. Like the probe 100, the feet extend from the workpiece facing surface by a thickness less than the seal 232. The additional feet in the probe 200 account for the fact that the user may apply pressure over different parts of the probe 200 (because it has no handles).

Unlike the probe 100, the probe 200 has a single fluid inlet 248, and channels within the body 216 provide fluid into the aperture 230 for ultrasonic coupling with the workpiece.

The invention claimed is:

1. An ultrasonic inspection probe comprising:
   a flexible ultrasonic array; and,
   a chassis arranged to hold the ultrasonic array in a predetermined position relative to the workpiece, the chassis having a first component defining a workpiece facing surface of the chassis and a second component defining a chassis loading surface of the chassis opposite thereto, the ultrasonic array disposed in the chassis between the workpiece facing surface and the chassis loading surface;
   the first and second components being releasably attached for insertion and removal of the ultrasonic array therebetween in which the chassis defines an aperture in the workpiece facing surface to provide a clear line of sight from the array to the workpiece.

2. An ultrasonic inspection probe according to claim 1, in which the workpiece facing surface and the first and second components are at least partially curved.

3. An ultrasonic inspection probe according to claim 2, in which the first and second components clamp the ultrasonic array therebetween.

4. An ultrasonic inspection probe according to claim 3, in which the first and second components are configured to be snap-fitted together.

5. An ultrasonic inspection probe according to claim 1, in which the aperture is surrounded by a deformable sealing material.

6. An ultrasonic inspection probe according to claim 5, in which the sealing material is a closed cell foam.

7. An ultrasonic inspection probe according to claim 1, in which the chassis defines couplant channels arranged to direct liquid couplant to the workpiece facing surface.

8. An ultrasonic inspection probe comprising:
a flexible ultrasonic array; and,
a chassis arranged to hold the ultrasonic array in a predetermined position relative to the workpiece, the chassis having a workpiece facing surface and a chassis loading surface opposite thereto, the ultrasonic array disposed in the chassis between the workpiece facing surface and the chassis loading surface;
in which the chassis defines an aperture in the workpiece facing surface, the aperture disposed between the ultrasonic array and the workpiece to provide a clear line of sight between the array and the workpiece.

9. An ultrasonic inspection probe according to claim 8, comprising a liquid injection system configured to direct liquid couplant to the aperture.

10. An ultrasonic inspection probe according to claim 9, in which the liquid injection system comprises a series of channels formed in the chassis.

11. An ultrasonic inspection probe according to claim 10, in which the liquid injection system comprises a series of outlets exiting into the aperture.

12. An ultrasonic inspection probe according to claim 8, in which the aperture is surrounded by a seal configured to seal against the workpiece in use.

13. An ultrasonic inspection probe according to claim 12, in which the seal is an endless loop surrounding the aperture.

14. An ultrasonic inspection probe according to claim 13, in which the seal is constructed from an closed cell foam.

15. An ultrasonic inspection probe comprising:
a flexible ultrasonic array; and,
a chassis arranged to hold the ultrasonic array in a predetermined position relative to the workpiece, the chassis having a main body defining a workpiece facing surface and a chassis loading surface opposite thereto, the ultrasonic array disposed in the main body between the workpiece facing surface and the chassis loading surface;
in which the chassis has at least one foot protruding from the workpiece facing surface of the main body in which the at least one foot is configured to provide an offset between the workpiece facing surface and workpiece in use.

16. An ultrasonic inspection probe according to claim 15, in which the at least one foot is constructed from a material having a lower coefficient of friction than the main body.

17. An ultrasonic inspection probe comprising:
a flexible ultrasonic array; and,
a chassis arranged to hold the ultrasonic array in a predetermined position relative to the workpiece, the chassis having a main body defining a workpiece facing surface and a chassis loading surface opposite thereto, the ultrasonic array disposed between the workpiece facing surface and the chassis loading surface;
in which the chassis has at least one foot protruding from the workpiece facing surface of the main body;
in which the chassis has a seal member protruding from the workpiece facing surface of the main body, the seal member arranged to seal against a workpiece in use, wherein a thickness of the foot normal to the workpiece facing surface is less than a thickness of the seal member such that the sealing material is compressed against the workpiece in use.

18. An ultrasonic inspection probe according to claim 17, in which the seal member is an endless loop defining a cavity between the workpiece facing surface and workpiece in use.

* * * * *